United States Patent
Takei (10) Patent No.: US 9,053,172 B2
(45) Date of Patent: Jun. 9, 2015

(54) MEDICAL IMAGE PROCESSING APPARATUS, PROGRAM, AND MEDICAL APPARATUS

(71) Applicants: KABUSHIKI KAISHA TOSHIBA, Tokyo (JP); Toshiba Medical Systems Corporation, Otawara-shi (JP)

(72) Inventor: Koji Takei, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 153 days.

(21) Appl. No.: 13/750,382

(22) Filed: Jan. 25, 2013

(65) Prior Publication Data

US 2013/0198200 A1 Aug. 1, 2013

(30) Foreign Application Priority Data

Jan. 30, 2012 (JP) .................................. 2012-017036
Nov. 15, 2012 (JP) .................................. 2012-251080

(51) Int. Cl.
*G06F 17/30* (2006.01)
*G06F 19/00* (2011.01)

(52) U.S. Cl.
CPC ........ *G06F 17/30619* (2013.01); *G06F 19/321* (2013.01); *G06F 17/30268* (2013.01)

(58) Field of Classification Search
CPC ......... G06F 19/32; G06F 17/30; G06Q 50/22; G06Q 50/24; G09B 5/00
USPC ........ 382/128; 705/2; 707/E17.014, E17.019, 707/E17.044, 741, 758, 999.003, 999.1; 709/217; 715/239
See application file for complete search history.

(56) References Cited

U.S. PATENT DOCUMENTS

| | | | |
|---|---|---|---|
| 6,424,996 B1 * | 7/2002 | Killcommons et al. | 709/206 |
| 7,373,600 B2 * | 5/2008 | Lee et al. | 715/239 |
| 7,620,643 B2 * | 11/2009 | Erhard et al. | 1/1 |
| 2006/0056680 A1 * | 3/2006 | Stutsman et al. | 382/154 |
| 2006/0239394 A1 * | 10/2006 | Fujieda | 378/1 |
| 2006/0242148 A1 * | 10/2006 | Rothpearl et al. | 707/7 |

(Continued)

FOREIGN PATENT DOCUMENTS

| | | |
|---|---|---|
| CN | 101286200 A | 10/2008 |
| JP | 2008-33665 A | 2/2008 |

(Continued)

OTHER PUBLICATIONS

Combined Chinese Office Action and Search Report issued Aug. 11, 2014 in Patent Application No. 201310036373.X with English Translation.

*Primary Examiner* — Dennis Truong
(74) *Attorney, Agent, or Firm* — Oblon, McClelland, Maier & Neustadt, L.L.P.

(57) ABSTRACT

According to one embodiment, a medical image processing apparatus includes a reception unit, determination unit, dividing unit, processing control unit, and storage processing unit. The reception unit receives first data including supported and unsupported tags, and individual data added to the supported or unsupported tag. The determination unit determines whether a tag included in the first data is supported or not. The dividing unit divides the first data into second data and third data. The processing control unit executes data processing by referring to the second data. The storage processing unit generates fourth data by adding second data to data acquired by the processing.

11 Claims, 6 Drawing Sheets

(56) References Cited

U.S. PATENT DOCUMENTS

| | | | |
|---|---|---|---|
| 2007/0041647 A1* | 2/2007 | Florin et al. | 382/233 |
| 2007/0203748 A1* | 8/2007 | Rothpearl et al. | 705/2 |
| 2009/0177637 A1* | 7/2009 | Hollebeek | 707/3 |
| 2009/0185729 A1* | 7/2009 | Matsue et al. | 382/128 |
| 2012/0233194 A1* | 9/2012 | Ohyu et al. | 707/758 |
| 2012/0311088 A1* | 12/2012 | Heere et al. | 709/217 |
| 2013/0198200 A1* | 8/2013 | Takei | 707/741 |

FOREIGN PATENT DOCUMENTS

| | | |
|---|---|---|
| JP | 2008-293371 A | 12/2008 |
| JP | 2009-172017 | 8/2009 |
| JP | 2009-193356 A | 8/2009 |
| WO | WO 2010/085899 A1 | 8/2010 |

\* cited by examiner

First data

| Tag | | VR | Data size | Actual data |
|---|---|---|---|---|
| 0x0010 | 0x0010 | X | x1 | Actual data 1 |
| 0x0010 | 0x0011 | X | x2 | Actual data 2 |
| 0x0010 | 0x0012 | X | x3 | Actual data 3 |

MEDICAL IMAGE PROCESSING APPARATUS, PROGRAM, AND MEDICAL APPARATUS

CROSS-REFERENCE TO RELATED APPLICATIONS

This application is based upon and claims the benefit of priority from Japanese Patent Applications No. 2012-017036, filed Jan. 30, 2012; and No. 2012-251080, filed Nov. 15, 2012, the entire contents of all of which are incorporated herein by reference.

FIELD

Embodiments described herein relate generally to a medical image processing apparatus, program, and medical apparatus.

BACKGROUND

Medical facilities conventionally use various medical apparatuses such as medical image processing apparatuses including medical image diagnostic apparatuses and image reference apparatuses, RIS (Radiology Information System) servers, and image servers. These medical apparatuses communicate with each other in compliance with, for example, the DICOM (Digital Imaging and Communication Medicine) standards.

For example, a medical image diagnostic apparatus such as an X-ray CT apparatus or MRI apparatus communicates with an RIS server in compliance with the DICOM standards to receive information concerning a captured image of an object from the RIS server. The medical image diagnostic apparatus captures an image of the object by referring to the received information. The medical image diagnostic apparatus communicates with the image server in compliance with the DICOM standards to transmit the captured medical image to the imager server.

Note that the data communicated in compliance with the DICOM standards includes individual data and a tag added to the individual data. The individual data includes patient information such as a patient name, patient ID, and sex. The tag is an identifier for identifying the attribute of the individual data. The DICOM standards include modes such as DICOM MWM and DICOM Storage meeting various needs. In addition, various types of medical apparatuses communicate with each other in compliance with the DICOM standards. For this reason, some individual data and some tags have unique information described for each mode, each medical apparatus, and each user.

As described above, since various kinds of information are described in individual data and tags, some individual data and some tags which are supported by a communication source medical apparatus may not be supported by a communication destination medical apparatus. In such a case, the operator of the communication source medical apparatus manually makes settings so as not to transmit any individual data or tags which are not supported by the communication destination medical apparatus or manually makes settings to delete individual data and tags which are not supported by this medical apparatus. This imposes heavy burden on the operator.

It is therefore an object to provide a medical image processing apparatus which can execute data processing concerning an object while reducing burden on the operator when, for example, the data received in compliance with the DICOM standards includes individual data and a tag which are not supported by the apparatus, and a program used by the apparatus. It is also object to provide a medical apparatus which can reduce burden on the operator when the data received in compliance with the DICOM standards includes individual data and a tag which are not supported by the apparatus.

DETAILED DESCRIPTION

In general, according to one embodiment, a medical image processing apparatus includes a reception unit, determination unit, dividing unit, processing control unit, and storage processing unit. The reception unit receives first data including at least a supported tag supported by the apparatus, individual data including patient information added to the supported tag, an unsupported tag which is not supported by the apparatus, and individual data to which the unsupported tag is added. The determination unit determines whether a tag included in the received first data is a supported tag or an unsupported tag. The dividing unit divides the first data into second data including individual data added to the supported tag and excluding individual data added to the unsupported tag and third data including at least individual data added to the unsupported tag and stores the second data in the first storage unit. The processing control unit executes data processing concerning an object by referring to the individual data included in the second data. The storage processing unit generates fourth data by adding second data including the referred individual data to data acquired by the processing and records the generated fourth data on the first storage unit.

An embodiment will be described below with reference to the accompanying drawing.

Figure 1:
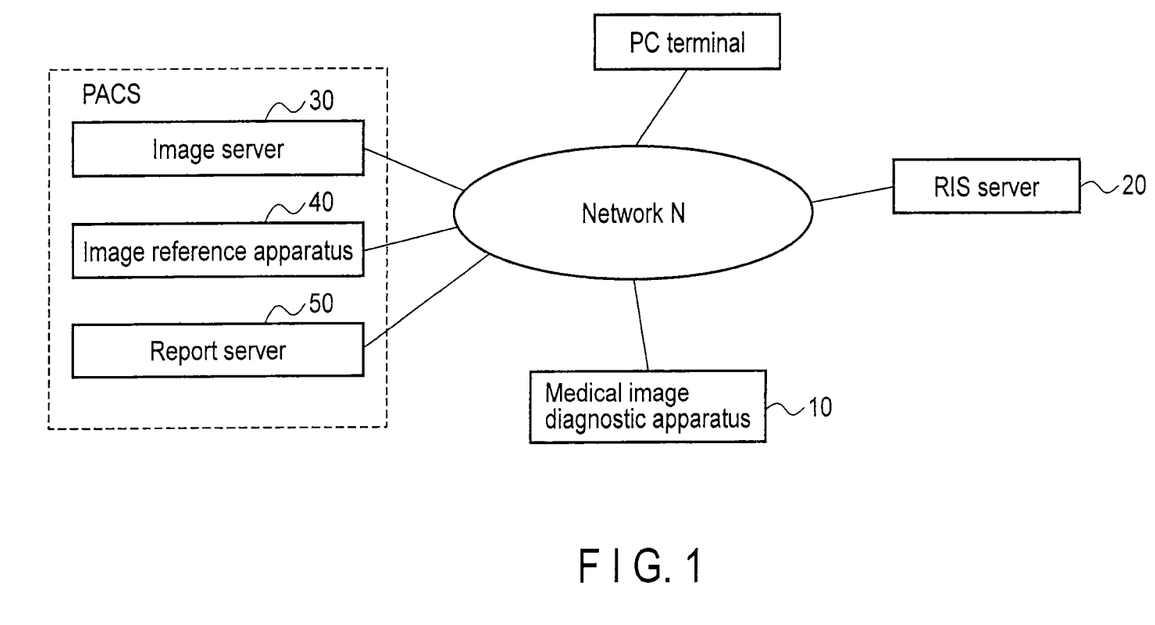
FIG. 1 is a block diagram showing the arrangement of a medical information system using a medical apparatus according to this embodiment.

FIG. 1 is a block diagram showing the arrangement of a medical information system using a medical apparatus according to this embodiment. In the medical information system shown in FIG. 1, various types of medical apparatuses and the PC terminal used by a primary doctor are arranged on a network N.

The medical information system shown in FIG. 1 includes, as examples of medical apparatuses, a medical image diagnostic apparatus 10, an RIS (Radiology Information System) server 20, an image server 30, an image reference apparatus 40, and a report server 50. Note that the medical image diagnostic apparatus 10 and the image reference apparatus 40 belong to medical image processing apparatuses.

The medical image diagnostic apparatus 10 is, for example, an X-ray CT apparatus, ultrasonic diagnostic apparatus, or MRI apparatus. The medical image diagnostic apparatus 10 receives information concerning a captured image of an object (patient information such as a a patient name, patient ID, and sex, and order information including a diagnostic region) from the RIS server 20 and generates a medical image by imaging the object by referring to the information.

The RIS server 20 manages information concerning radiographic examination operation. That is, the RIS server 20 accepts a radiographic examination request from the RIS terminal (not shown) and generates information concerning a captured image of the object by referring to this radiographic examination request. The RIS server 20 transmits the generated information to the medical image diagnostic apparatus 10.

The image server 30, the image reference apparatus 40, and the report server 50 constitute a PACS (Picture Archiving and Communication System). The image server 30 archives the medical image generated by the medical image diagnostic apparatus 10, and outputs the archived medical image in accordance with the request. The image reference apparatus 40 displays the medical image archived in the image server 30, and makes the operator generate an interpretation report concerning the displayed medical image. The report server 50 archives the generated interpretation report and outputs the archived interpretation report in accordance with a request.

The medical image diagnostic apparatus 10 as the above medical apparatus, the RIS server 20, the image server 30, the image reference apparatus 40, and the report server 50 communicate with each other in compliance with the DICOM (Digital Imaging and Communication Medicine) standards. An X-ray CT apparatus as the medical image diagnostic apparatus 10 will be described in detail below as an example of a medical apparatus complying with the DICOM standards.

Figure 2:
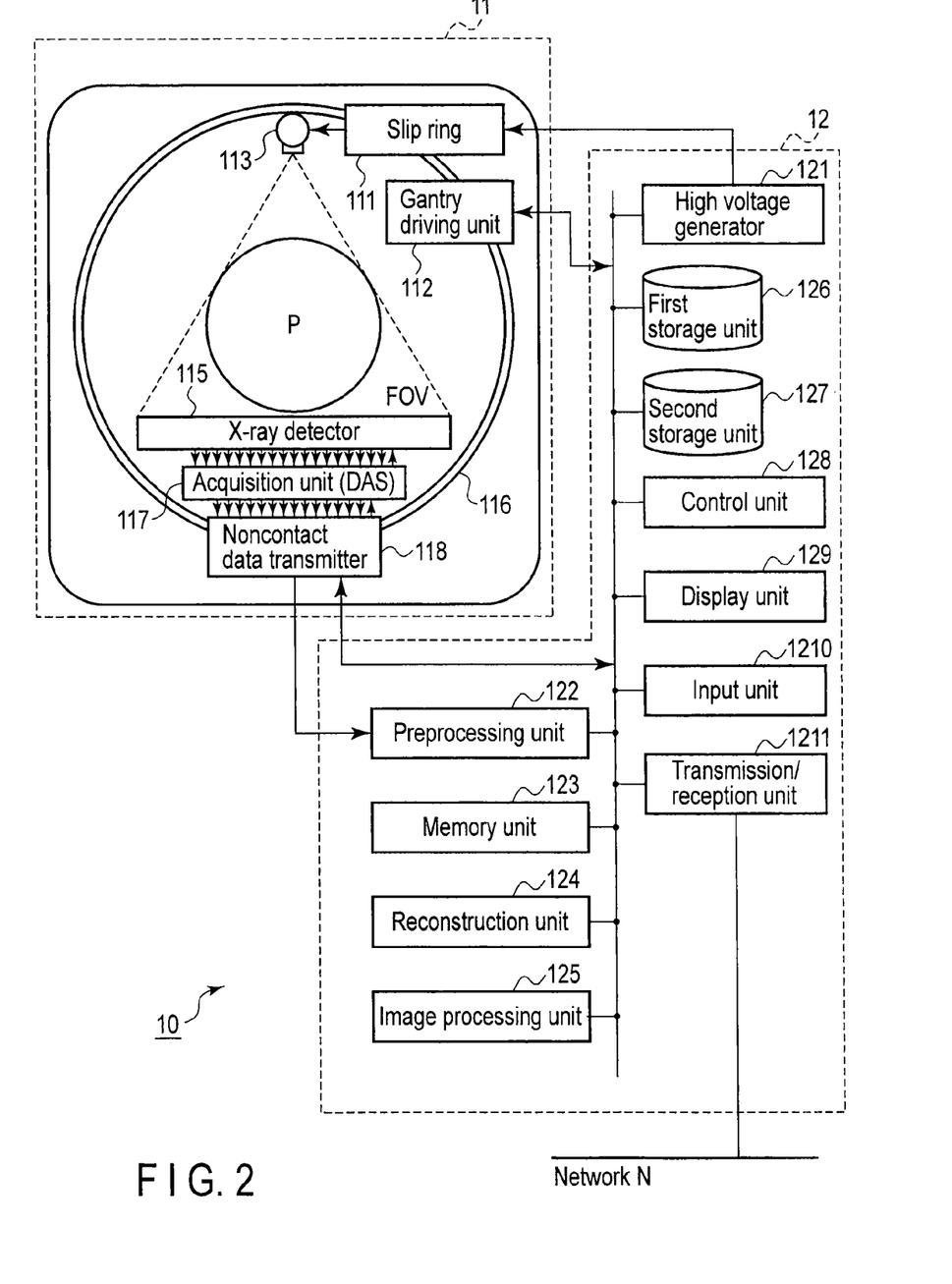
FIG. 2 is a block diagram showing the functional arrangement of the medical image diagnostic apparatus shown in FIG. 1.

FIG. 2 is a block diagram showing the functional arrangement of the medical image diagnostic apparatus 10 according to this embodiment. The medical image diagnostic apparatus 10 in FIG. 2 includes a gantry 11 and an information processing unit 12.

The gantry 11 is configured to acquire projection data concerning an object P. The gantry 11 includes a slip ring 111, a gantry driving unit 112, an X-ray tube 113, an X-ray detector 115, a rotating frame 116, a data acquisition unit 117, and a noncontact data transmitter 118.

The information processing unit 12 controls the data acquiring operation on the gantry 11 and performs predetermined processing for the data acquired on the gantry 11 to generate an X-ray CT image and various kinds of clinical information using the image. The information processing unit 12 includes a high voltage generator 121, a preprocessing unit 122, a memory unit 123, a reconstruction unit 124, an image processing unit 125, a first storage unit 126, a second storage unit 127, a control unit 128, a display unit 129, an input unit 1210, and a transmission/reception unit 1211.

The gantry driving unit 112 rotates and drives the rotating frame 116. With this rotating/driving operation, the X-ray tube 113 and the X-ray detector 115 helically rotate about the body axis of the object P while facing each other.

The X-ray tube 113 is a vacuum tube which generates X-rays, and is provided on the rotating frame 116. The high voltage generator 121 supplies power (a tube current and a tube voltage) necessary for the emission of X-rays to the X-ray tube 113 via the slip ring 111. The X-ray tube 113 emits X-rays to the object P placed in an effective field of view FOV by accelerating electrons with the applied high voltage and making them collide with a target.

The X-ray detector 115 is a detector system which detects the X-rays transmitted through the object, and is mounted on the rotating frame 116 so as to face the X-ray tube 113. The X-ray detector 115 is a single-slice type or multi-slice type detector, which has a plurality of detection elements, each constituted by a pair of a scintillator and a photodiode, arrayed one-dimensionally or two-dimensionally in accordance with each type.

The rotating frame 116 is a ring which is rotated/driven about the Z-axis, and on which the X-ray tube 113 and the X-ray detector 115 are mounted. An opening is formed in the central portion of the rotating frame 116. The object P placed on a bed (not shown) is inserted in the opening portion.

The acquisition unit 117 is generally called a DAS (Data Acquisition System), which converts the signal output from the data acquisition circuit 115 for each channel into a voltage signal, amplifies it, and converts it into a digital signal. This data (raw data) is input to the information processing unit 12 via the noncontact data transmitter 118.

The high voltage generator 121 is a device which supplies power necessary for the emission of X-rays to the X-ray tube 113 via the slip ring 111, and is constituted by a high voltage transformer, filament heating converter, rectifier, high voltage switch, and the like.

The preprocessing unit 122 receives raw data from the acquisition unit 117 via the noncontact data transmitter 118, and executes sensitivity correction and X-ray intensity correction. The first storage unit 126 temporarily stores the raw data corresponding to 360° which has undergone various types of correction. Note that the raw data preprocessed by the preprocessing unit 122 will be referred to as "projection data".

The reconstructing unit 124 is equipped with a plurality of types of reconstruction methods and reconstructs image data by the reconstruction method selected by the operator. The plurality of reconstruction methods include, for example, (i) fan beam reconstruction methods (also called fan beam convolution/back projection methods), (ii) the Feldkamp method as an approximate image reconstruction method in which a projection ray obliquely crosses a reconstruction plane, in which a projection ray is regarded as a fan projection beam in convolution on the premise that the cone angle is small, and in which a reverse projection is processed along a scan ray, and (iii) a cone beam reconstruction method as a method which suppresses cone angle errors more than the Feldkamp method, in which projection data is corrected in accordance with the angle of a ray with respect to a reconstruction plane.

The image processing unit 125 performs image processing for display such as window conversion and RGB processing for the reconstructed image data generated by the reconstruction unit 124, and outputs the resultant data to the display unit 129. In addition, the image processing unit 125 generates a so-called pseudo three-dimensional image such as a tomographic image of an arbitrary slice, a projection image from an arbitrary direction, or a three-dimensional surface image, and outputs the image to the display unit 129 in accordance with instructions from the operator.

The display unit 129 is an output device which displays CT images such as computer tomographic images and scanograms supplied from the image processing unit 125. In this case, a CT value is the X-ray absorption coefficient of a substance which is expressed as a relative value with respect to a reference substance (e.g., water). The display unit 129 displays an unsupported tag list generated by the control unit 128 (to be described later). The display unit 129 displays the scan plan window or the like implemented by a plan support system (not shown).

The input unit 1210 is a device which includes a keyboard, various kinds of switches, and a mouse and allows to input various kinds of scan conditions such as a slice thickness and the number of slices via the operator.

The transmission/reception unit 1211 communicates with other medical apparatuses in compliance with the DICOM standards via a network N to transmit/receive image data, patient information, and the like. In particular, the transmission/reception unit 1211 receives information concerning a captured image of the object from the RIS server 20 connected to the network N. The transmission/reception unit 1211 transmits the acquired medical image to the image server 30 connected to the network N.

Figure 3:
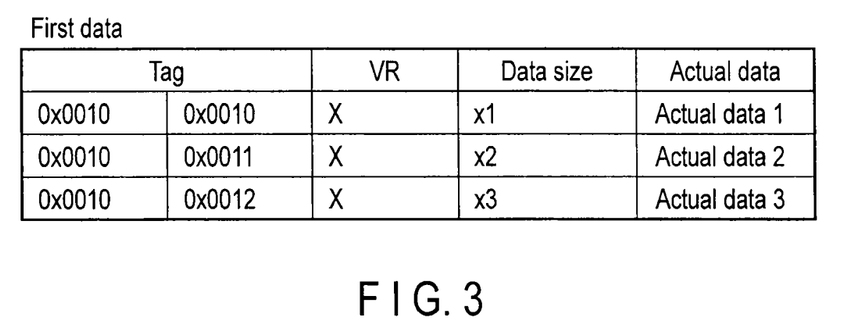
FIG. 3 is a view showing an example of the first data transmitted from the RIS server shown in FIG. 1 to the medical image diagnostic apparatus.

FIG. 3 is a view schematically showing an example of data (to be referred to as the first data hereinafter) transmitted from the RIS server 20 to the medical image diagnostic apparatus 10 in compliance with the DICOM standards. The first data includes a plurality of data elements. Each data element includes a tag, VR, data size, and actual data. A tag is an identifier for identifying the attribute of a data element. A data size indicates the size of actual data. Actual data is patient information such as a patient name, patient ID, sex. A VR, data size, and actual data will be referred to as individual data hereinafter. Note that a VR may not exist depending on the form of DICOM standards. Note that the first data exists for each patient. That is, if a plurality of patient exist, the first data exist in correspondence with the number of patients.

In addition to a CPU (Central Processing Unit), the control unit 128 includes, for example, storage areas storing programs for the execution of processing by the CPU and data, such as a ROM (Read Only Memory) and a RAM (Random Access Memory). The control unit 128 implements the functions of the respective processing units shown in FIG. 4 by making the CPU execute dedicated programs. That is, the control unit 128 shown in FIG. 4 includes a determination unit 1281, a dividing unit 1282, a storage processing unit 1283, an imaging control unit 1284, a search unit 1285, a combining unit 1286, and a list generating unit 1287.

Figure 4:
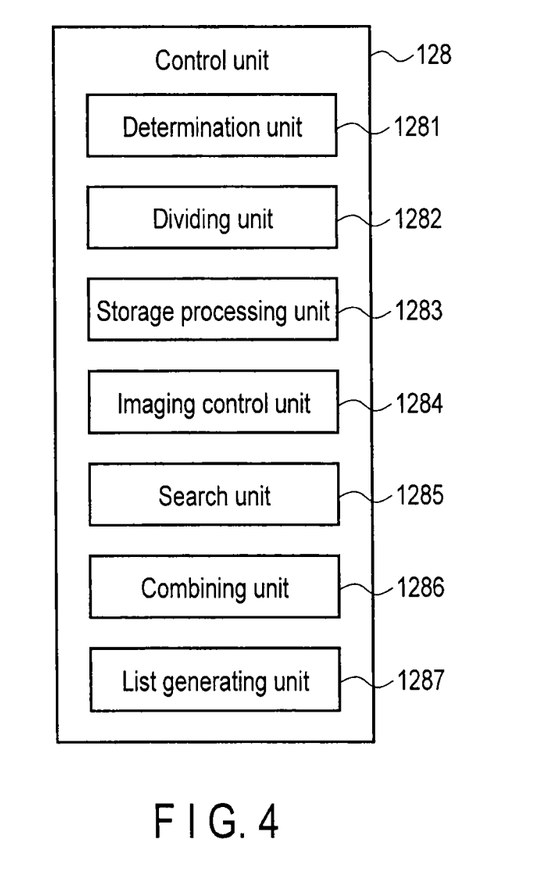
FIG. 4 is a block diagram showing the functional arrangement of the control unit shown in FIG. 2.

The determination unit 1281 compares a tag included in the first data received from the RIS server 20 via the transmission/reception unit 1211 with the supported tag list. The determination unit 1281 stores the supported tag list in advance, in which a tag added to individual data which can be used by the medical image diagnostic apparatus 10 is described. The determination unit 1281 compares a tag included in the first data with the supported tag list to determine whether the tag included in the first data is a supported tag supported by the self apparatus or an unsupported tag which is not supported by the self apparatus. In the present invention, "unsupported tag" is intended to refer to a tag that has not yet been supported.

Figure 5:
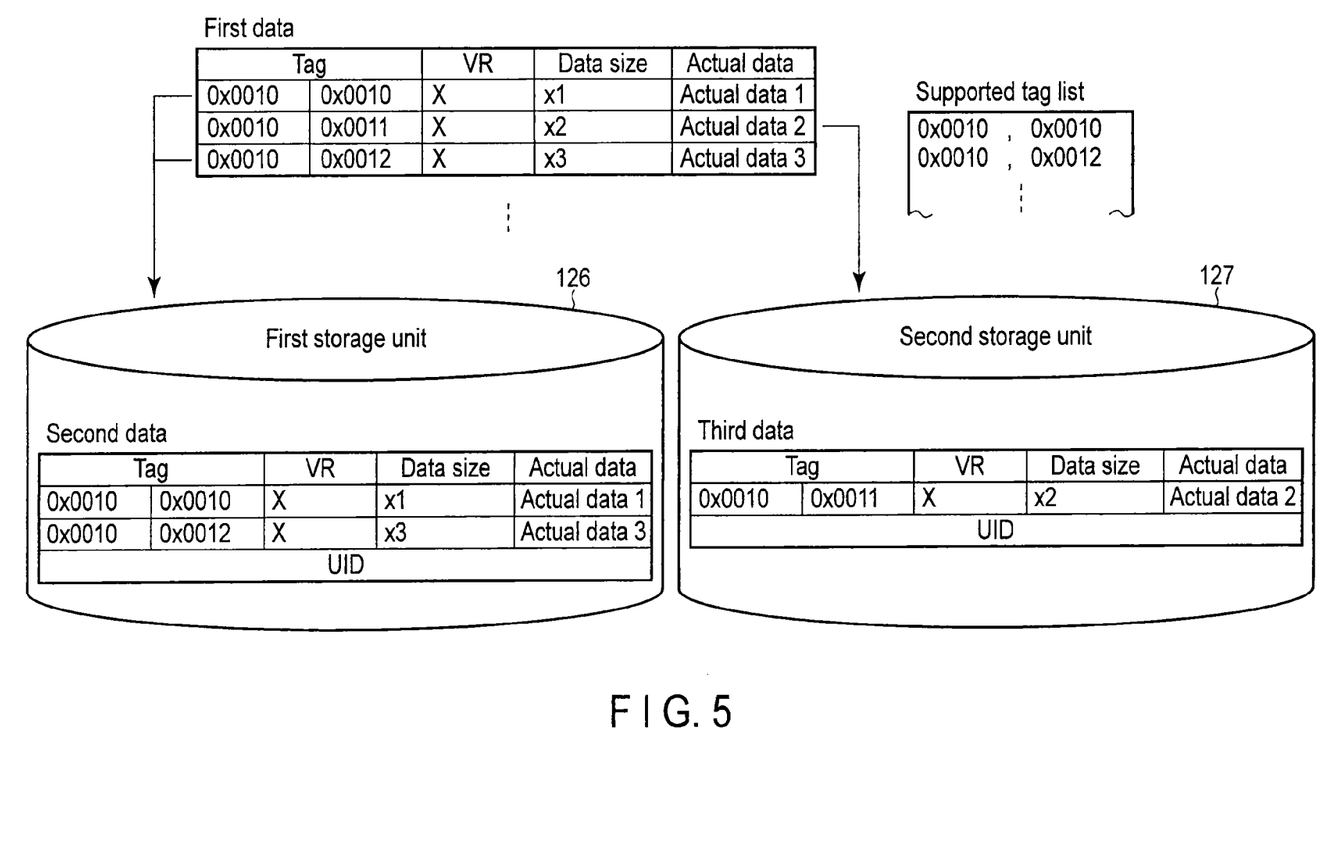
FIG. 5 is a view showing an example of how the control unit shown in FIG. 4 stores the first data in the first and second storage units.

FIG. 5 is a schematic view showing an example how the control unit 128 stores the first data in the first and second storage units 126 and 127. Referring to FIG. 5, tag 1: (0x0010, 0x0010) and tag 3: (0x0010, 0x0012) are included in the supported tag list, and tag 2: (0x0010, 0x0011) is not included in the supported tag list. The determination unit 1281 determines that tags 1 and 3 are supported tags, and tag 2 is an unsupported tag.

The dividing unit 1282 divides the first data by referring to the determination result obtained by the determination unit 1281. For example, the dividing unit 1282 divides the first data into: a supported tag and individual data to which the supported tag is added; and an unsupported tag and individual data to which the unsupported tag is added. At this time, the dividing unit 1282 adds identical UIDs (Unique IDs) to the supported tag and the individual data to which the supported tag is added and to the unsupported tag and the individual data to which the unsupported tag is added, which are divided from the first data. The data obtained by adding the UID to the supported tag and the individual data to which the supported tag is added will be referred to as second data in the following description. The data obtained by adding the UID to the unsupported tag and the individual data to which the unsupported tag is added will be referred to as third data in the following description. Adding the identical UIDs to the second and third data associate them with each other. Note that the UID may be described in the first data in advance. If no UID is described in advance, the dividing unit 1282 may generate a UID. A UID is, for example, a Study Instance UID, Series Instance UID, or SOP Instance UID.

For example, referring to FIG. 5, the dividing unit 1282 divides the first data into: tags 1 and 3 as supported tags and individual data 1 and 3 to which the tags are added; and tag 2 as an unsupported tag and individual data 2 to which tag 2 is added. The dividing unit 1282 adds a UID to tags 1 and 3 and individual data 1 and 3 to generate the second data, and adds a UID to tag 2 and individual data 2 to generate the third data.

The storage processing unit 1283 stores the second data in the first storage unit 126, and stores the third data in the second storage unit 127. When storing image data such as raw data, projection data, scanogram data, or tomographic image data, which is obtained under the control of the imaging control unit 1284, in the first storage unit 126, the storage processing unit 1283 generates fourth data by adding the second data including the individual data referred to at the time of imaging to the acquired image. The storage processing unit 1283 stores the generated fourth data in the first storage unit 126.

Figure 6:
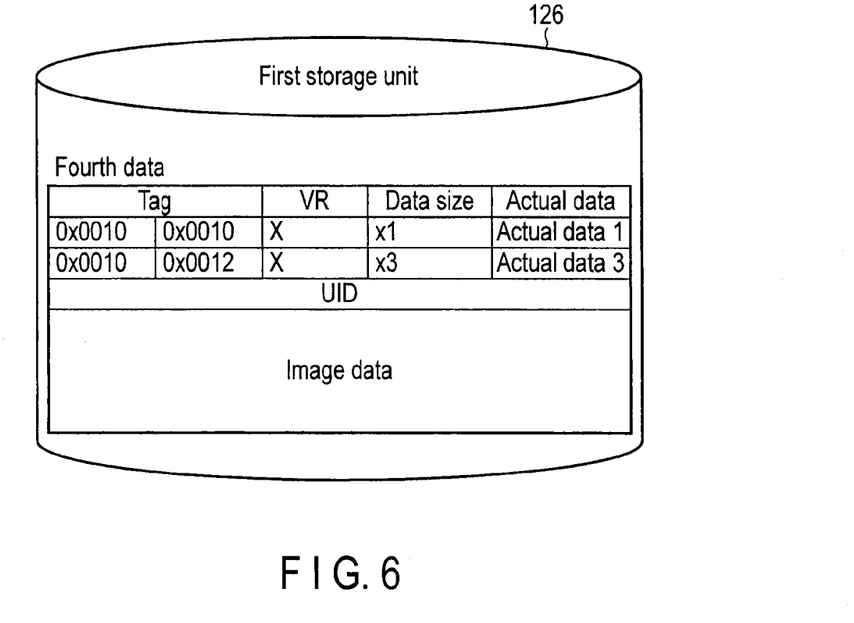
FIG. 6 is a view showing an example of the fourth data stored in the first storage unit shown in FIG. 2.

For example, referring to FIG. 5, the storage processing unit 1283 stores tags 1 and 3, individual data 1 and 3, and UID as the second data in the first storage unit 126, and stores tag 2, individual data 2, and UID as the third data in the second storage unit 127. FIG. 6 is a schematic view showing an example of the fourth data stored in the first storage unit 126. Referring to FIG. 6, the image data is stored in the first storage unit 126 upon being added with tags 1 and 3, individual data 1 and 3, and UID. Although FIG. 6 exemplifies the case in which tags 1 and 3, individual data 1 and 3, and UID are added to the image data, the image data is actually further added with, for example, data including conditions used for imaging operation and a tag for identifying the attribute of the data, in addition to tags 1 and 3, individual data 1 and 3, and UID.

The imaging control unit 1284 comprehensively controls X-ray CT image capturing processing in the medical image diagnostic apparatus 10 in scan processing, signal processing, image generation processing, image display processing, and the like by referring to the tags and individual data included in the second data stored in the first storage unit 126. For example, in scan processing, the imaging control unit 1284 sets scan conditions in accordance with the patient ID, slice thickness, and the like included in individual data, controls the feed amounts and feed rates of the high voltage generator 121, gantry driving unit 112, and bed top in the body axis direction, the rotational speeds and rotational pitches of the X-ray tube 113 and X-ray detector 115, an X-ray emission timing, and the like based on the scan conditions, and irradiates a desired imaging region of the object with X-ray cone beams or X-ray fan beams from many directions, thereby acquiring (scanning) X-ray CT image data.

When the medical image diagnostic apparatus 10 receives an instruction to transmit an acquired medical image to the image server 30 or the like, the search unit 1285 searches the second storage unit 127 for the third data including the same UID as that included in the fourth data stored in the first storage unit 126.

Figure 7:
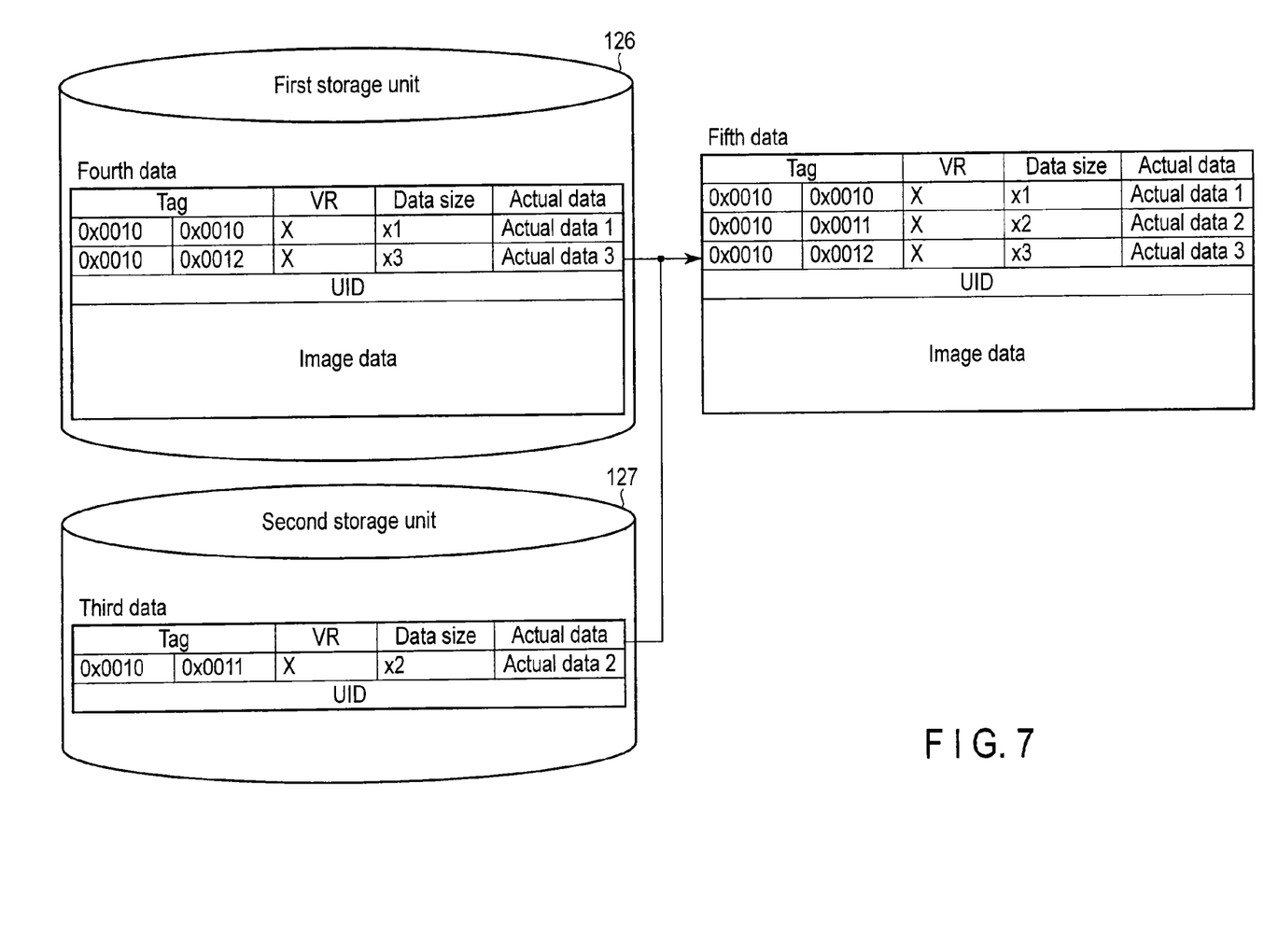
FIG. 7 is a view showing an example of the fifth data generated by the combining unit shown in FIG. 4.

The combining unit 1286 reads out the fourth data from the first storage unit 126 and reads out the third data acquired by the search from the second storage unit 127. The combining unit 1286 generates the fifth data by combining the readout fourth and third data. FIG. 7 is a schematic view of the fifth data generated by the combining unit 1286. Referring to FIG. 7, the combining unit 1286 reads out tags 1 and 3, individual data 1 and 3, UID, and image data from the first storage unit 126. The combining unit 1286 reads out tag 2, individual data 2, and UID from the second storage unit 127. The combining unit 1286 combines the readout data to generate the fifth data including tags 1 to 3, individual data 1 to 3, UID, and image data. The transmission/reception unit 1211 transmits the fifth data to the image server 30 or the like.

Figure 8:
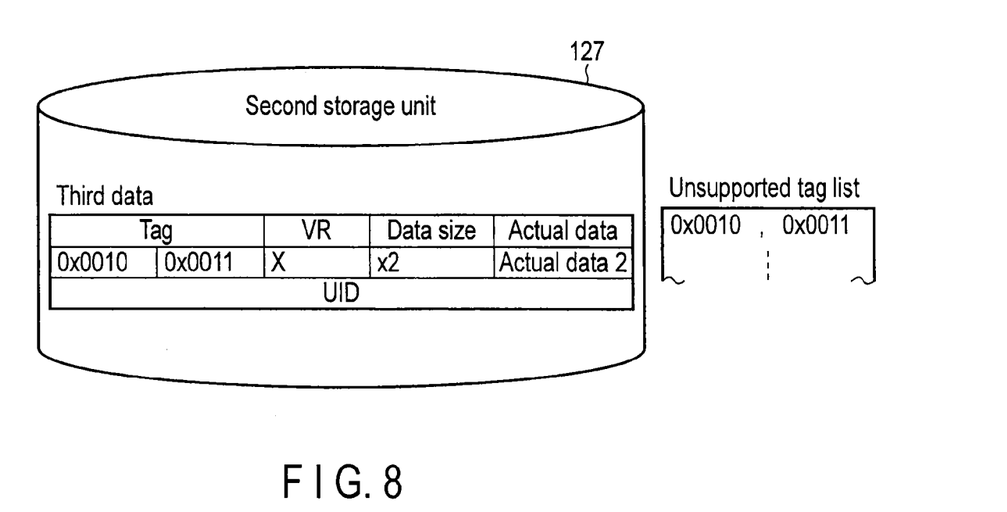
FIG. 8 is a view showing an example of the supported tag list generated by the list generating unit shown in FIG. 4.

The list generating unit 1287 generates an unsupported tag list by referring to the tag included in the third data stored in the second storage unit 127. If an unsupported tag list is generated, the list generating unit 1287 updates the unsupported tag list by referring to the tag included in the third data stored in the second storage unit 127. FIG. 8 is a schematic view showing an example of the supported tag list generated by the list generating unit 1287.

As described above, in the above embodiment, the determination unit 1281 and the dividing unit 1282 divide the data to be transmitted in compliance with the DICOM standards into the second data including a supported tag and individual data to which the supported tag is added and the third data including an unsupported tag and individual data to which the unsupported tag is added. The imaging control unit 1284 acquires the image data of the object by referring to the second data. The storage processing unit 1283 generates the fourth data by adding the second data including the individual data referred to at the time of imaging to the image data, and stores the generated fourth data in the first storage unit 126. This makes it unnecessary for the operator to manually remove the tag and individual data which are not supported by the self apparatus from the received first data. The medical image diagnostic apparatus 10 then images the object by referring to the supported tag and individual data included in the first data.

If the size of the received first data is large because it includes an unsupported tag and individual data to which the unsupported tag is added, the conventional medical image diagnostic apparatus may not be able to perform imaging operation even though it can receive a request to perform imaging operation. This is because, since the conventional medical image diagnostic apparatus cannot discriminate a supported tag from an unsupported tag, the captured image data is added to the first data, and the data size after the acquisition of the image data exceeds the storage capacity of the medical image diagnostic apparatus. In contrast, the medical image diagnostic apparatus 10 according to this embodiment extracts only a supported tag and the like upon discriminating the supported tag and the like from an unsupported tag and the like, even if the size of the first data is large because it includes the unsupported tag and the individual data to which the unsupported tag is added, and stores the necessary data in the first storage unit 126. For this reason, the data size after the acquisition of the image data, i.e., the data size of the fourth data, does not exceed the storage capacity of the medical image diagnostic apparatus 10. Even if, therefore, the medical image diagnostic apparatus 10 receives the first data whose size is large because it includes an unsupported tag and individual data to which the unsupported tag is added, it is possible to avoid the interruption of imaging of the object.

In this embodiment, when the medical image diagnostic apparatus 10 receives an instruction to transmit an acquired medical image to the image server 30 or the like, the search unit 1285 searches the second storage unit 127 for the third data associated with the fourth data including the medical image. The combining unit 1286 generates the fifth data by combining the fourth data with the third data acquired by the search. If the received first data includes private data unique to the communication source apparatus and many tags and individual data, the medical image diagnostic apparatus 10 preferably transmits these data together with image data upon acquisition of it. According to this embodiment, it is possible to generate the fifth data added with the image captured at this examination while maintaining all the tags and individual data included in the first data at the time of reception and transmit the fifth data to the image server 30 or the like.

In the above embodiment, the list generating unit 1287 generates an unsupported tag list by referring to the tag included in the third data stored in the second storage unit 127. This automatically updates a list of unsupported tags included in the first data received from another apparatus and hence improves the connectivity of the medical image diagnostic apparatus 10.

The medical image diagnostic apparatus 10 according to this embodiment can therefore image an object while reducing burden on the operator, when the data received in compliance with the DICOM standards includes individual data and a tag which are not supported by the self apparatus. That is, it is possible to execute data processing concerning the object while reducing burden on the operator.

Note that the above embodiment may be configured to be able to update a supported tag list. For example, when the medical image diagnostic apparatus 10 is updated, the number of supported tags may increase. In such a case, updating the supported tag list can cope with such updating of the medical image diagnostic apparatus 10.

The above embodiment has exemplified the case in which the received first data includes a supported tag, individual data to which the supported tag is added, an unsupported tag, and individual data to which the unsupported tag is added. However, the data included in the first data are not limited to them. For example, the first data may include image data.

The above embodiment has also exemplified the case in which the control unit 128 included in the medical image diagnostic apparatus 10 processes the first data received in compliance with the DICOM standards. However, the embodiment is not limited to this. For example, medical apparatuses such as the image server 30, the image reference apparatus 40, and the report server 50 may include a control unit which performs the same processing as that performed by the control unit 128.

For example, a case in which the image reference apparatus 40 includes a control unit which performs the same processing as that performed by the control unit 128 will be described. The image reference apparatus 40 receives the first data including image data. The image reference apparatus 40 divides the first data into: the second data including a supported tag, individual data to which the supported tag is added, and image data; and the third data including an unsupported tag and individual data to which the unsupported tag is added. The image reference apparatus 40 generates an interpretation report concerning the image data included in the second data by using the processing control function of the control unit based on operation by the operator of the image reference apparatus 40. The image reference apparatus 40 generates the fourth data by combining the generated interpretation report and the like with the second data. The image reference apparatus 40 generates the fifth data by combining the generated fourth data with the third data corresponding to the fourth data.

The above embodiment has exemplified the case in which the medical apparatus performs communication complying with the DICOM standards. However, the embodiment is not limited to this. For example, the medical apparatus may perform communication complying with standards other than the DICOM standards as long as the standards take the same data structure as that of the first data.

Furthermore, the above embodiment has exemplified the case in which the dividing unit 1282 divides the first data into: a supported tag and individual data to which the supported tag is added; and an unsupported tag and individual data to which the unsupported tag is added. However, the embodiment is not limited to this. For example, the dividing unit 1282 divides the first data into the second data including a supported tag and individual data to which the supported tag is added. The third data divided from the first data at this time may include an unsupported tag and individual data to which the unsupported tag is added, and at least one of a supported tag and individual data to which the supported tag is added.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
a receiver configured to receive first data including at least a supported tag supported by the apparatus, individual data including patient information added to the supported tag, an unsupported tag which is not supported by the apparatus, and individual data to which the unsupported tag is added; and
a processor configured to
determine whether a tag included in the received first data is a supported tag or an unsupported tag;
divide the first data into second data including individual data added to the supported tag and excluding individual data added to the unsupported tag and third data including at least individual data added to the unsupported tag and store the second data in a first memory;
execute data processing concerning an image of an object by referring to the individual data included in the second data; and
generate fourth data by adding second data including the referred individual data to image data acquired by the processing and record the generated fourth data on the first memory.

2. The apparatus of claim 1, wherein the processor is further configured to:
add identical unique IDs (UIDs) to the second data and the third data,
store the third data in a second memory,
generate fifth data by combining the fourth data stored in the first memory with the third data stored in the second memory based on the UIDs,
the apparatus further comprising a transmitter configured to transmit the fifth data.

3. The apparatus of claim 1, wherein the processor is further configured to generate an unsupported tag list based on an unsupported tag included in third data stored in the second memory.

4. The apparatus of claim 1, wherein the processor is further configured to determine whether a tag included in the received first data is a supported tag or an unsupported tag by referring to a supported tag list in which a supported tag is described.

5. The apparatus of claim 1, wherein the processor is further configured to
image an object by referring to individual data included in the second data, and
generate the fourth data by adding the second data including the referred individual data to image data obtained by the imaging, and record the generated fourth data in the first memory.

6. The apparatus of claim 1, wherein the processor is further configured to
generate data concerning the image of the object by referring to individual data included in the second data, and
generate the fourth data by adding second data including the referred individual data to the generated data, and record the generated fourth data in the first memory.

7. The apparatus of claim 1, wherein the receiver is configured to receive the first data, which exists for each patient.

8. The apparatus of claim 2, wherein the processor is further configured to
associate the second data and the third data which are divided from same first data with each other by adding the UIDs,
search the second memory for the third data associated with second data included in the fourth data based on the UIDs, and
generate the fifth data by combining the third data acquired by the search with the fourth data.

9. A non-transitory computer-readable storage medium comprising a program used by a computer included in a medical image processing apparatus which receives first data including at least a supported tag supported by the apparatus, individual data including patient information added to the supported tag, an unsupported tag which is not supported by the apparatus, and individual data to which the unsupported tag is added, the program causing the computer to execute:
a determination process of determining whether a tag included in the received first data is a supported tag or an unsupported tag;
a dividing process of dividing the first data into second data including individual data added to the supported tag and excluding individual data added to the unsupported tag and third data including at least individual data added to the unsupported tag, identical unique IDs (UIDs) being added to the second data and the third data;
a first recording process of recording the second data in a first memory;
a second recording process of recording the third data in a second memory;
an execution process of executing data processing concerning an image of an object by referring to the individual data included in the second data recorded in the first memory;

a third recording process of generating fourth data by adding second data including the referred individual data to data acquired by the data processing and recording the generated fourth data in the first memory; and a combining process of generating fifth data by combining the fourth data recorded in the first memory with the third data recorded in the second memory.

10. The computer-readable medium of claim 9, wherein the dividing process associates the second data and the third data divided from same first data with each other by adding the UIDs, the program further causes the computer to execute a search process of searching the second memory for the third data associated with the second data included in the fourth data, and the combining process generates the fifth data by combining the third data acquired by the search with the fourth data.

11. A medical apparatus, comprising:

a receiver configured to receive first data including at least a supported tag supported by the apparatus, individual data including patient information added to the supported tag, an unsupported tag which is not supported by the apparatus, and individual data added to the unsupported tag;

a first memory configured to store second data;

a second memory configured to store third data;

a processor configured to:

determine whether a tag included in the received first data is a supported tag or an unsupported tag;

divide the first data into second data including individual data of the supported tag and excluding individual data of the unsupported tag and third data including at least individual data of the unsupported tag, identical unique IDs (UIDs) being added to the second data and the third data;

store the second data in the first memory;

store the third data in the second memory;

search the second memory for the third data associated with the second data stored in the first memory based on the UIDs;

generate fifth data by combining the third data acquired by the search with the second data; and a transmitter configured to transmit the fifth data.

* * * * *